(12) United States Patent
Trudel et al.

(10) Patent No.: US 12,690,914 B2
(45) Date of Patent: Jul. 28, 2026

(54) POWER ESTIMATION OF DISTAL END OF ELECTROSURGICAL INSTRUMENT

(71) Applicant: Encision Inc., Boulder, CO (US)

(72) Inventors: Gregory J. Trudel, Fort Collins, CO (US); Kurt A. Aronow, Eldorado Springs, CO (US); Marek S. Newton, Lafayette, CO (US); David W. Newton, Longmont, CO (US)

(73) Assignee: Encision, Inc.

( * ) Notice: Subject to any disclaimer, the term of this patent is extended or adjusted under 35 U.S.C. 154(b) by 331 days.

(21) Appl. No.: 18/474,358

(22) Filed: Sep. 26, 2023

(65) Prior Publication Data

US 2025/0099165 A1     Mar. 27, 2025

(51) Int. Cl.
A61B 18/12          (2006.01)
A61B 18/14          (2006.01)
A61B 18/00          (2006.01)

(52) U.S. Cl.
CPC ...... A61B 18/1482 (2013.01); A61B 18/1206 (2013.01); *A61B 2018/00577* (2013.01); *A61B 2018/00589* (2013.01); *A61B 2018/00595* (2013.01); *A61B 2018/00601* (2013.01); *A61B 2018/00779* (2013.01); *A61B 2018/00827* (2013.01); *A61B 2018/00892* (2013.01)

(58) Field of Classification Search
CPC ............ A61B 18/1206; A61B 18/1233; A61B 18/1445; A61B 18/1482; A61B 18/16; A61B 2018/00178; A61B 2018/00577; A61B 2018/00589; A61B 2018/00595;

A61B 2018/00601; A61B 2018/00702; A61B 2018/00779; A61B 2018/00827; A61B 2018/00875; A61B 2018/00892; A61B 2018/00988
See application file for complete search history.

(56) References Cited

U.S. PATENT DOCUMENTS

| | | | | |
|---|---|---|---|---|
| 5,573,533 A | * | 11/1996 | Strul ................... | A61B 18/1492 607/101 |
| 5,702,386 A | * | 12/1997 | Stern .................. | A61B 18/1206 606/45 |
| 2002/0077645 A1 | * | 6/2002 | Wiener .......... | A61B 17/320068 606/169 |
| 2003/0236487 A1 | * | 12/2003 | Knowlton ............ | A61B 18/203 604/20 |
| 2006/0041253 A1 | * | 2/2006 | Newton ............. | A61B 18/1233 606/34 |

(Continued)

OTHER PUBLICATIONS

"International Search Report and Written Opinion", issued in corresponding International Application No. PCT/US24/46921; Dated Dec. 10, 2024.

*Primary Examiner* — Daniel W Fowler
(74) *Attorney, Agent, or Firm* — NOD Law PC

(57)          ABSTRACT

Power estimation of a distal end of an electrosurgical instrument. One embodiment is a system for performing an electrosurgical procedure, the system includes an electrosurgical generator, an electrosurgical instrument, and a monitor. The monitor determines one or more electrical characteristics of the electrosurgical instrument, estimates a real power output of the active electrode based on the determination of the one or more electrical characteristics, and displays the real power output of the active electrode.

16 Claims, 6 Drawing Sheets

(56)     References Cited

U.S. PATENT DOCUMENTS

2009/0112204  A1*    4/2009   Aronow  ............. A61B 18/1233
                                                          606/34
2015/0359584  A1*  12/2015   Newton  ............. A61B 18/1233
                                                          606/34
2016/0310202  A1*  10/2016   Wham  ............... A61B 18/1206
2017/0348041  A1   12/2017   Encision

* cited by examiner

300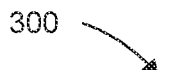

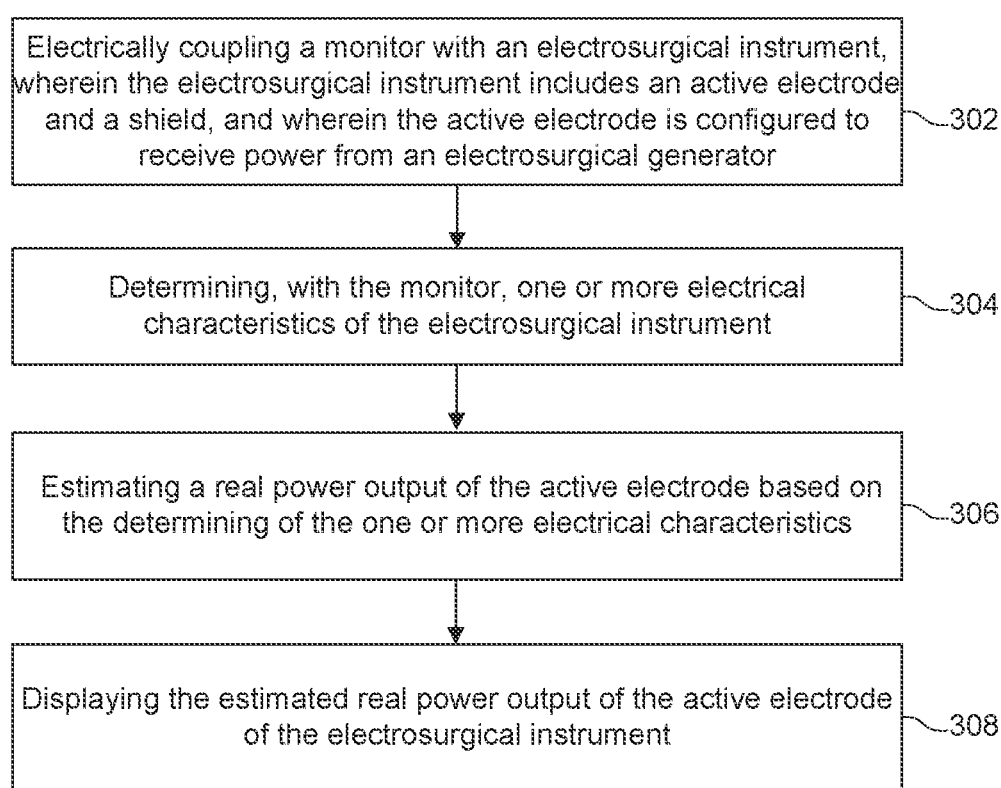

Electrically coupling a monitor with an electrosurgical instrument, wherein the electrosurgical instrument includes an active electrode and a shield, and wherein the active electrode is configured to receive power from an electrosurgical generator    ~302

Determining, with the monitor, one or more electrical characteristics of the electrosurgical instrument    ~304

Estimating a real power output of the active electrode based on the determining of the one or more electrical characteristics    ~306

Displaying the estimated real power output of the active electrode of the electrosurgical instrument    ~308

FIG. 3

POWER ESTIMATION OF DISTAL END OF ELECTROSURGICAL INSTRUMENT

TECHNICAL FIELD

The present disclosure relates generally to electrosurgical instruments, and in particular, to systems and methods for estimating power output at the distal end of an electrosurgical instrument.

BACKGROUND

In electrosurgery, laparoscopic instruments are often used to cut, coagulate, or ablate tissue using high-frequency electrical currents. The instrument has an active electrode that delivers electrical energy to the target tissue and may also have an outer shield or sheath that surrounds the active electrode. The shield is designed to provide high-frequency electrical grounding to the patient and safety during the procedure.

When the active electrode is energized, some electrical charge may be stored between the active electrode and the shield, creating a capacitance therebetween. Instrument capacitance to the shield can affect the performance and safety of the instrument during use. In addition, shield breakdown can lead to issues such as increased current leakage or stray electrical energy, which may cause unintended tissue damage or electrical interference with nearby electronic equipment. Typically, a monitor continuously looks for shield breakdown based on monitoring shield current.

Additionally, the overall capacitance of the instrument affects the power delivered to the active electrode during the electrical procedure. Power measurements cannot be taken directly at the active electrode because its small size cannot accommodate sensing components such as a resistor or a capacitive divider. A surgeon therefore relies on the power output setting of the generator as an approximate estimate of the power output at the instrument's active electrode. However, estimating in this way may be inaccurate because it does not account for a possible drop in real power due to the instrument cable and/or instrument capacitance to the shield. This is especially true for instruments having higher capacitances, such as those having longer cables and/or smaller diameters. Accordingly, there is continued need for techniques and systems which improve the accuracy of power delivered by an electrosurgical tool to a patient and which may improve the monitor performance.

SUMMARY

Embodiments described herein comprise systems and methods for accurately estimating the power provided by the active electrode of a surgical instrument.

One embodiment is a system for performing an electrosurgical procedure, the system includes an electrosurgical generator, and an electrosurgical instrument comprising an active electrode and a shield, wherein the active electrode receives power provided by the electrosurgical generator. The system also includes a monitor configured to be electrically coupled between the electrosurgical instrument and the electrosurgical generator, to determine one or more electrical characteristics of the electrosurgical instrument, to estimate a real power output of the active electrode based on the one or more electrical characteristics, and to display the real estimated power output of the active electrode of the electrosurgical instrument. The determination of the one or more electrical characteristics comprises one or more of: (1) measure an active voltage of the active electrode; (2) measure an active current of the active electrode; (3) measure a shield current of the shield; (4) measure a capacitance of the active electrode to the shield using a low-voltage capacitance measurement circuit that is switched in while the electrosurgical generator is not being keyed on; and (5) determine a capacitance (or equivalent) of the electrosurgical instrument based on a lookup table and a detected identifier of the electrosurgical instrument.

Another embodiment is an apparatus comprising a monitor configured to be electrically coupled between an electrosurgical instrument and an electrosurgical generator, wherein the electrosurgical instrument includes an active electrode and shield. The monitor includes one or more of: measurement circuitry configured to measure at least one of: an active voltage of the active electrode, an active current of the active electrode; capacitance measurement circuitry configured to measure a capacitance of the active electrode to the shield, wherein the capacitance measurement circuitry is configured to be switched in to an active line of the monitor while the electrosurgical generator is not being keyed on and a shield current of the shield; and identification circuitry configured to detect an identifier of the electrosurgical instrument, and to determine a parameter value corresponding with the identifier in a lookup table. The monitor includes a processor configured to determine an estimated real power output of the active electrode based on one or more of the active voltage, the active current, the shield current, and the parameter value. The monitor also includes a display device configured to display the estimated real power output of the active electrode of the electrosurgical instrument. Alternatively or additionally, the monitor may send the estimated real power value to the electrosurgical generator to be displayed or processed.

Another embodiment is a method of providing an accurate power estimate of a distal end of an electrosurgical instrument. The method includes electrically coupling a monitor with the electrosurgical instrument, wherein the electrosurgical instrument includes an active electrode and a shield, and wherein the active electrode is configured to receive power from an electrosurgical generator. The method also includes determining, with the monitor, one or more electrical characteristics of the electrosurgical instrument. The determining includes one or more of: measuring an active voltage of the active electrode, measuring an active current of the active electrode, measuring a shield current of the shield, and determining a parameter value of the electrosurgical instrument based on a lookup table and a detected identifier of the electrosurgical instrument. The method also includes estimating a real power output of the active electrode based on the one or more electrical characteristics, and displaying the real estimated power output of the active electrode of the electrosurgical instrument.

The above summary provides a basic understanding of some aspects of the specification. This summary is not an extensive overview of the specification. It is intended to neither identify key or critical elements of the specification nor delineate any scope particular embodiments of the specification, or any scope of the claims. Its sole purpose is to present some concepts of the specification in a simplified form as a prelude to the more detailed description that is presented later.

DESCRIPTION OF THE DRAWINGS

Some embodiments of the present disclosure are now described, by way of example only, and with reference to the accompanying drawings. The same reference number represents the same element or the same type of element on all drawings.

FIG. 3 is a flowchart illustrating a method of providing an accurate power estimate of a distal end of an electrosurgical instrument in an example embodiment.

DETAILED DESCRIPTION

The figures and the following description illustrate specific exemplary embodiments. It will thus be appreciated that those skilled in the art will be able to devise various arrangements that, although not explicitly described or shown herein, embody the principles of the embodiments and are included within the scope of the embodiments. Furthermore, any examples described herein are intended to aid in understanding the principles of the embodiments, and are to be construed as being without limitation to such specifically recited examples and conditions. As a result, the inventive concept(s) is not limited to the specific embodiments or examples described below, but by the claims and their equivalents.

Figure 1:
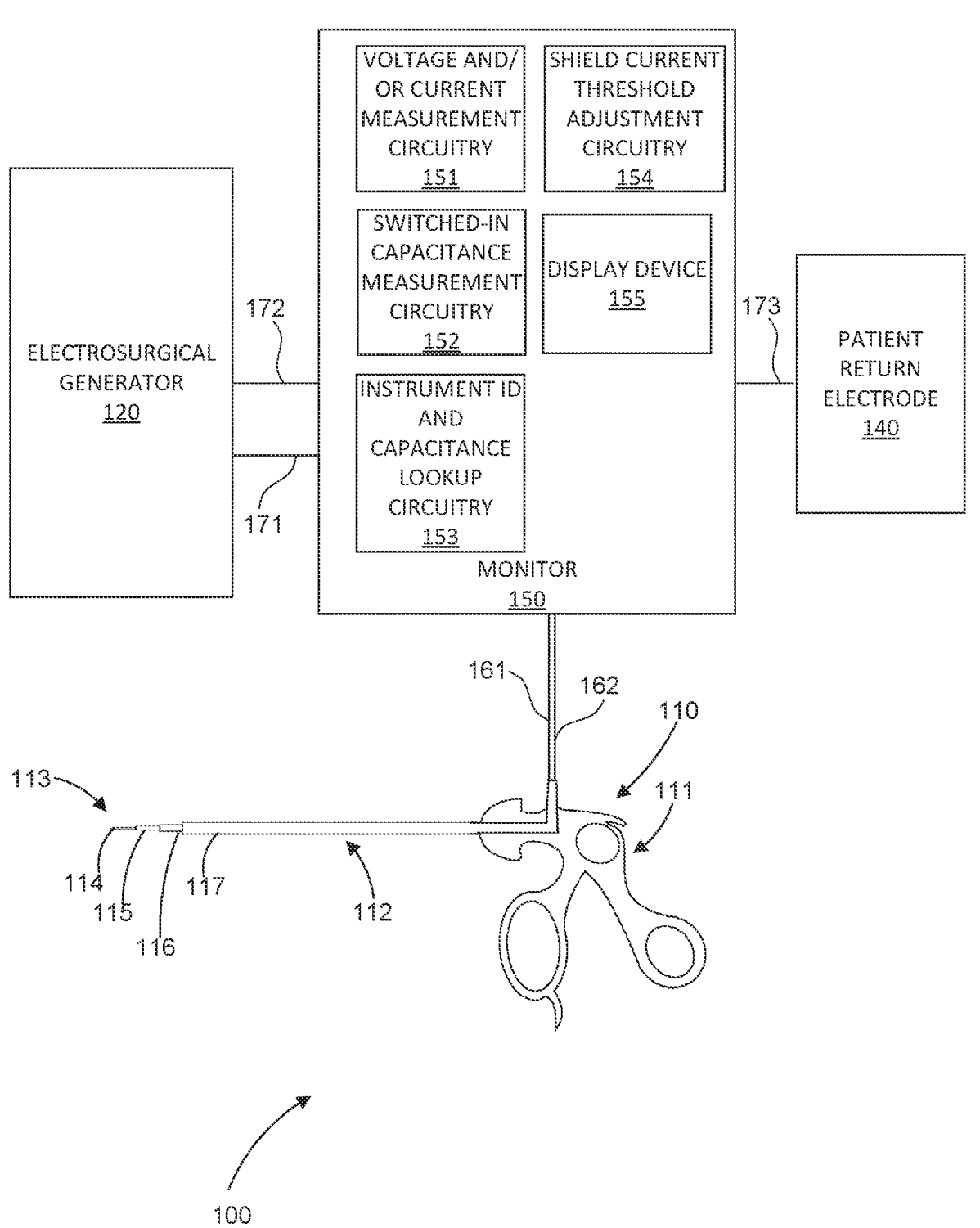
FIG. 1 is a diagram of a surgical system in an example embodiment.

FIG. 1 is a diagram of a surgical system 100 in an example embodiment. The surgical system 100 includes an electrosurgical instrument 110, an electrosurgical generator 120, and a monitor 150. In general, the electrosurgical instrument 110 is configured to perform a surgical procedure on a patient. For example, the electrosurgical instrument 110 may comprise a handheld device, such as a laparoscopic tool, used by a surgeon to perform an electrosurgical task such as cutting, coagulation, ablation, or cauterization.

In one embodiment, the electrosurgical instrument 110 includes a handle assembly 111 and a tube assembly 112. The handle assembly 111 may comprise, for example, graspers, scissors, dissectors, or other specialized surgical tools. The tube assembly 112 is physically coupled or attached with the handle assembly 111 and facilitates insertion and manipulation of the instrument during the surgical procedure. In particular, the tube assembly 112 includes a distal end 113 (sometimes referred to as an active electrode 114, tip, probe, or end effector) which may have a particular shape (e.g., needle-shape, hook-shape, spatula-shape, scissors, etc.) to serve the desired surgical function. The distal end 113 may be inserted into a patient's body through a trocar or port, providing access to the surgical area while minimizing incision size. In one embodiment, the tube assembly 112 includes the active electrode 114, a dielectric insulator 115, a shield 116, and an outer insulating sheath 117.

Power is supplied to the electrosurgical instrument 110 by the electrosurgical generator 120. The electrosurgical generator 120 is configured to generate high-frequency electrical signals to provide the electrical energy for cutting, coagulation, or other electrosurgical tasks. For example, the electrosurgical generator 120 typically generates signals in the radio frequency (RF) range (e.g., between 50 KHz to 5 MHz), but the type of generator implemented may vary depending upon the type of electrosurgical procedure being performed.

The monitor 150 is configured to detect faults in the electrosurgical instrument 110. More particularly, the monitor 150 may continuously monitor a current flowing through the electrosurgical instrument 110 during an electrosurgical procedure to detect any abnormalities or deviations indicating a current fault. The monitor 150 may also detect over-current situations in which the electrical current exceeds safe limits, indicating potential issues such as short circuits, excessive loads, or faults within the electrical circuit. Current faults may result from various issues, such as capacitive coupling, insulation failure, and patient leakage current.

Capacitive coupling occurs when there is unintended electrical coupling between the active electrode 114 and shield 116 or other nearby conductive structures. Insulation failure occurs when there is a breach in the electrical insulation (e.g., dielectric insulator 115) between the active electrode 114 and the instrument's shaft or other conductive components. Patient leakage current is current that flows from the active electrode 114 to the patient's body via unintended pathways other than the target tissue. Each of these issues may cause stray currents or unintended energy delivery to non-target areas and pose a safety risk to the patient.

The monitor 150 is therefore typically equipped to trigger one or more safety mechanisms in response to detecting an electrical issue such as a current fault. For example, the monitor 150 may generate visual or audible alarms to alert the surgical team of a potential issue. Alternatively or additionally, the monitor 150 may automatically shut down or reduce power output of the electrosurgical generator 120 to mitigate risk and protect the patient.

The monitor 150 is also configured to be coupled with a patient return electrode 140. The patient return electrode 140 is typically a large adhesive pad placed on the patient's skin at a location away from the surgical site. It provides an electrical return path from the patient's body back to the electrosurgical generator 120 via electrical cables 172-173, completing the electrical circuit. The connection is made to an appropriate input terminal on the electrosurgical generator 120 for proper grounding and safety during the procedure.

The monitor 150 is therefore configured to be electrically coupled to the electrosurgical instrument 110, the electrosurgical generator 120, and the patient return electrode 140. In particular, the monitor 150 may be operatively coupled to the electrosurgical instrument 110 via an active electrode cable 161 (sometimes referred to as an active line) and a shield current return cable 162 which may couple to the patient return electrode 140. The active electrode cable 161 and the shield current return cable 162 may be enclosed by a common sheath (not shown) to simplify cable management. The cables may sometimes be referred to as wires or wiring.

In some embodiments, the monitor 150 is configured to couple the active electrode cable 161 to the electrosurgical generator 120 via an active cable link 171, which may be a short cable or any other connecting mechanism suitable for the high currents and voltages expected, including a manual switching mechanism or integral pin and socket mechanism. The active cable link 171 provides a means for operatively coupling the monitor 150 to any one of a variety of electrosurgical generators 120, which may not be standardized across the industry. However, it should be understood that any electrical coupling between the monitor 150, electrosurgical generator 120, patient return electrode 140, and/or electrosurgical instrument 110 may be employed, including, but not limited to, male plugs, female plugs, male jacks, female jacks or any other suitable mating system. Alternatively or additionally, the monitor 150 may be integrated entirely or partially with the electrosurgical generator 120. As such, in some embodiments, components/functionality of the monitor 150 and generator 120 may be combined, and the active electrode 114 may directly couple with the generator 120 via one or more electrical cables.

As previously mentioned, when the active electrode 114 is energized, some electrical charge may be stored between the active electrode 114 and the shield, 116 creating a capacitance therebetween. This so-called instrument capacitance to the shield affects the performance and safety of the electrosurgical instrument 110 during use. Moreover, the capacitance of the electrosurgical instrument 110 and its cable(s) can affect power output of the active electrode 114. For instance, capacitance to the shield can result in energy leakage or diversion from the active electrode to unintended areas, causing a decrease in power delivery to the target tissue. Capacitance of a cable can cause signal loss, attenuation, and phase shift, especially for high-frequency signals used in electrosurgery, causing signal degradation and reduced power transfer efficiency. Moreover, capacitance of the cable can lead to voltage drop along the length of the cable, reducing the voltage available at the active electrode 114.

To address the above-described issues, the monitor 150 is enhanced with functionality to accurately estimate a power drop caused by the capacitance of the electrosurgical instrument 110 and associated cables. The estimated power drop enables the monitor 150 to accurately estimate the power being provided at the active electrode 114 to the patient. Advantageously, the monitor 150 can provide a real-time display of accurate power estimation of the instrument's distal end to the surgical team during a procedure.

In one embodiment, the monitor 150 includes one or more of voltage and/or current measurement circuitry 151, switched-in capacitance measurement circuitry 152, instrument identification and capacitance lookup circuitry 153, shield current threshold adjustment circuitry 154, and a display device 155. The voltage and/or current measurement circuitry 151 is configured to measure one or more of an active voltage of the active electrode 114, an active current of the active electrode 114, and a shield current of the shield 116. The switched-in capacitance measurement circuitry 152 is configured to measure a capacitance of the active electrode 114 to the shield 116. This circuitry may comprise a low-voltage circuit that is switched onto the active line after the electrosurgical generator 120 is turned off (i.e., not being keyed).

The instrument identification and capacitance lookup circuitry 153 is configured to identify the electrosurgical instrument 110 or the type of instrument, and reference its identity in a lookup table to determine a capacitance (or equivalent) value associated with the instrument. Accordingly, in addition to or as an alternative to estimating power output of the active electrode 114 using one or more electrical property measurements as described above, the monitor 150 may determine an estimated power output of the active electrode 144 based on a capacitive value corresponding with a detected identifier of the electrosurgical instrument 110 in a lookup table.

The monitor 150 may also advantageously include functionality for improving operation of the surgical system 100 using the accurate estimation of power output of the active electrode 114. In one embodiment, the shield current threshold adjustment circuitry 154 is configured to adjust a fault trip threshold for the shield current of the electrosurgical instrument based on the estimated power output of the active electrode 114. Previous monitors typically use a fixed shield current threshold, and when the fixed value is exceeded, the instrument is assumed to have at least a soft short circuit. By contrast, shield current threshold adjustment circuitry 154 advantageously allows the threshold, which determines when the instrument is no longer usable, to be appropriately adjusted in the monitor 150 according to an estimated amount of capacitance of the instrument and cable. For instance, the monitor 150 may thus automatically take into account higher-capacitance instruments and cables to avoid unnecessary fault triggers and improve surgical operation.

The monitor 150 may also include a display device 155 configured to display the estimated power output of the active electrode 114 of the electrosurgical instrument 110. The display device 150 may include any suitable device for displaying a power value to the surgical team. The display device 150 may be integrated in the monitor 150 and/or electrosurgical generator 120 (e.g., in embodiments in which monitor 150 and electrosurgical generator 120 are integrated). Alternatively or additionally, the monitor 150 may be configured to communicate power values and/or display data to one or more external devices for display thereon. In one embodiment, the monitor 150 sends the estimated real power output/value to the electrosurgical generator 120 to be displayed or processed. In some embodiments, the electrosurgical generator 120 is configured to process the estimated real power value to automatically compensate for a reduction in power due to capacitive loading.

Figure 2:
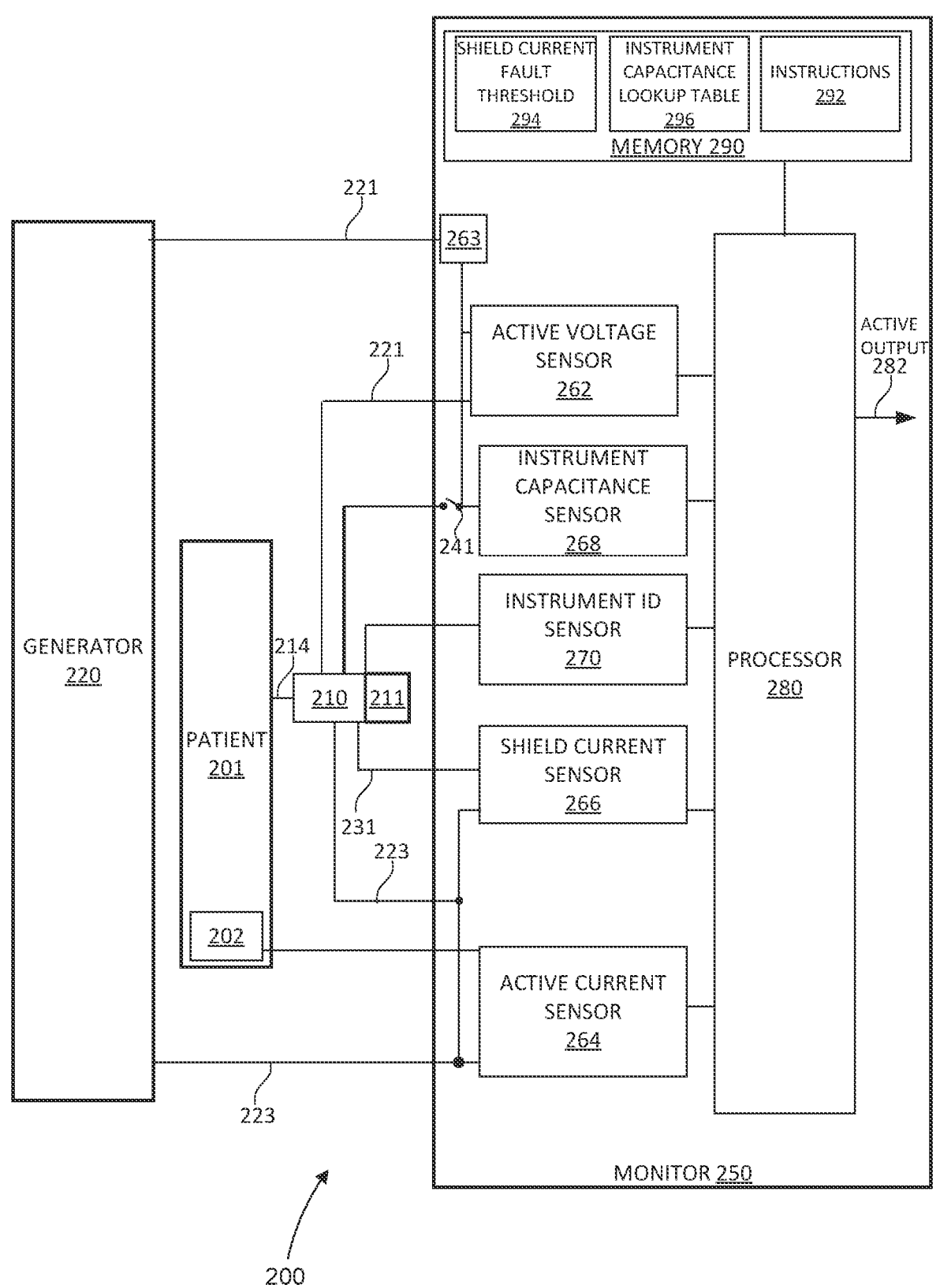
FIG. 2 is a block diagram of a surgical system in another example embodiment.

FIG. 2 is a block diagram of a surgical system 200 in another example embodiment. Components described with respect to FIG. 2 shows example components of a monitor 250 and electrical connections thereof and with a generator 220, patient return electrode 202 of a patient 201, and electrosurgical instrument 210 and cable 211. In one embodiment, the monitor 250 includes one or more of an active voltage sensor 262, active current sensor 264, and shield current sensor 266. Active sensors 262-264 electrically couple respective active lines 221/223 of the generator 220 with the active electrode 214 of the electrosurgical instrument 210. Shield current sensor 266 electrically couples with a shield of the electrosurgical instrument 210 via a shield line 231. In some embodiments, the monitor 250 includes a relay 263 on an active line (e.g., active line 221) configured to interrupt power to the electrosurgical instrument 210.

The active voltage sensor 262 is configured to measure active voltage, active current sensor 264 is configured to measure active current, and shield current sensor 266 is configured to measure shield current. The sensors 262-266 may comprise differential capacitive dividers, filters, op amps, analog-digital converters (ADCs), and/or other electrical components to carry out the described functions. The sensors 262-266 may be configured to contemporaneously or simultaneously sense the active voltage, active current, and shield current. In some embodiments, the active current is used as a means of recording and or displaying power and current delivered to the patient 201 and may or may not be used for fault detection.

Alternatively or additionally, the monitor 250 includes an instrument capacitance sensor 268. The instrument capacitance sensor 268 is configured to be switched onto an active line (e.g., active line 221) after the electrosurgical generator 120 is turned off or cutoff (e.g., via relay 263). The instrument capacitance sensor 268 is configured to measure a capacitance of the active electrode 114 to the shield 116 while a low voltage is supplied to the active electrode 114. The instrument capacitance sensor 268 is switchably coupled to the electrosurgical instrument 210 via a switch 241 (e.g., a relay).

Although not shown in FIG. 2 for ease of illustration, switch 241 and relay 263 may be coupled with logic or processing components to direct their operation according to the functionality described herein. Still further, in some embodiments, the monitor 250 includes an instrument identification sensor 270. The instrument identification sensor 270 is configured detect an identifier of the electrosurgical instrument, and to determine a capacitive value corresponding with the identifier in a lookup table.

The monitor 250 also includes one or more processors 280 and a memory 290. Processor 280 represents the internal circuitry, logic, hardware, etc., that provides the functions of the monitor 250. Processor 280 may be configured to execute instructions 292 (i.e., computer program code) for software that are loaded into memory 290. Processor 280 may comprise a set of one or more processors or may comprise a multi-processor core, depending on the particular implementation. For example, the processor 280 may include one or more Central Processing Units (CPU), Graphics Processing Units (GPU), microprocessors, Digital Signal Processors (DSPs), Application-specific Integrated Circuits (ASICs), Programmable Logic Devices (PLD or FPGA), control circuitry, etc. Some examples of processors include INTEL® CORE™ processors, Advanced Reduced Instruction Set Computing (RISC) Machines (ARM®) processors, etc.

Memory 290 is a computer readable storage medium for data, instructions 292, applications, etc., and is accessible by processor 280. Memory 290 is a hardware storage device capable of storing information on a temporary basis and/or a permanent basis. Memory 290 may comprise volatile or non-volatile Random-Access Memory (RAM), Read-Only Memory (ROM), FLASH devices, volatile or non-volatile Static RAM (SRAM) devices, magnetic disk drives, Solid State Disks (SSDs), or any other volatile or non-volatile storage device. Memory 290 may also be incorporated into the processor or FPGA.

The sensors 262-270 pass the monitored shield current, active current, active voltage, and/or capacitance lookup to the processor 280. Using one or more of these inputs, the processor 280 may estimate a power drop of the electrosurgical instrument 210 and/or the power being provided at the active electrode 114 (shown in FIG. 1). In one embodiment, the processor 280 is configured to calculate power drop due to one or more electrical characteristics of the electrosurgical instrument 110 (shown in FIG. 1, e.g., reactive power drop due to shield capacitance). The processor 280 may then determine the power output of the active electrode 114 by taking into account the determined power drop from a power output value determined and/or communicated from the generator 220. Alternatively or additionally, the processor 280 is configured to determine the estimated real power output of the active electrode 114 by multiplying the active voltage and the active current together on a continuous basis (or sampled on a regular or periodic basis) and calculating an average or Root Mean Square of the multiplication result to estimate the real power at the active electrode tip. An active output 282 of the processor 280 passes visible and/or audible indications of the monitor status to a surgeon, operator or other user. In some embodiments, the processor 280 continuously receives the inputs and adapts the active output 282 to the changing conditions or sensed values/parameters.

The active output 282 may also be used to adjust values in memory 290. For example, a shield current fault threshold 294 may be stored in memory 290. The processor 280 may dynamically update the stored shield current fault threshold 294 based on processing input to improve, for example, the operation of high-capacitance instruments. Memory 290 may also store an instrument capacitance lookup table 296. The processor 290 may reference the instrument capacitance lookup table 296 based on the detected identity of an instrument/cable plugged-in to a panel of the monitor 250 and/or generator 220. The processor 280 may also update an entry in the lookup table 296 based on a recent or periodic measurement taken for a particular instrument. Further illustrative details are described below.

FIG. 3 is a flowchart illustrating a method of providing an accurate power estimate of a distal end of an electrosurgical instrument in an example embodiment. The steps of the method 300 are described with reference to the surgical system 100 of FIG. 1, but those skilled in the art will appreciate that the method 300 may be performed in other systems. The steps of the flowcharts described herein are not all inclusive, may include other steps not shown, and may be performed in an alternative order.

In step 302, a monitor 150 is electrically coupled with an electrosurgical instrument 110, wherein the electrosurgical instrument 110 includes an active electrode 114 and a shield 116, and wherein the active electrode 114 is configured to receive power from an electrosurgical generator 120.

Figure 4:
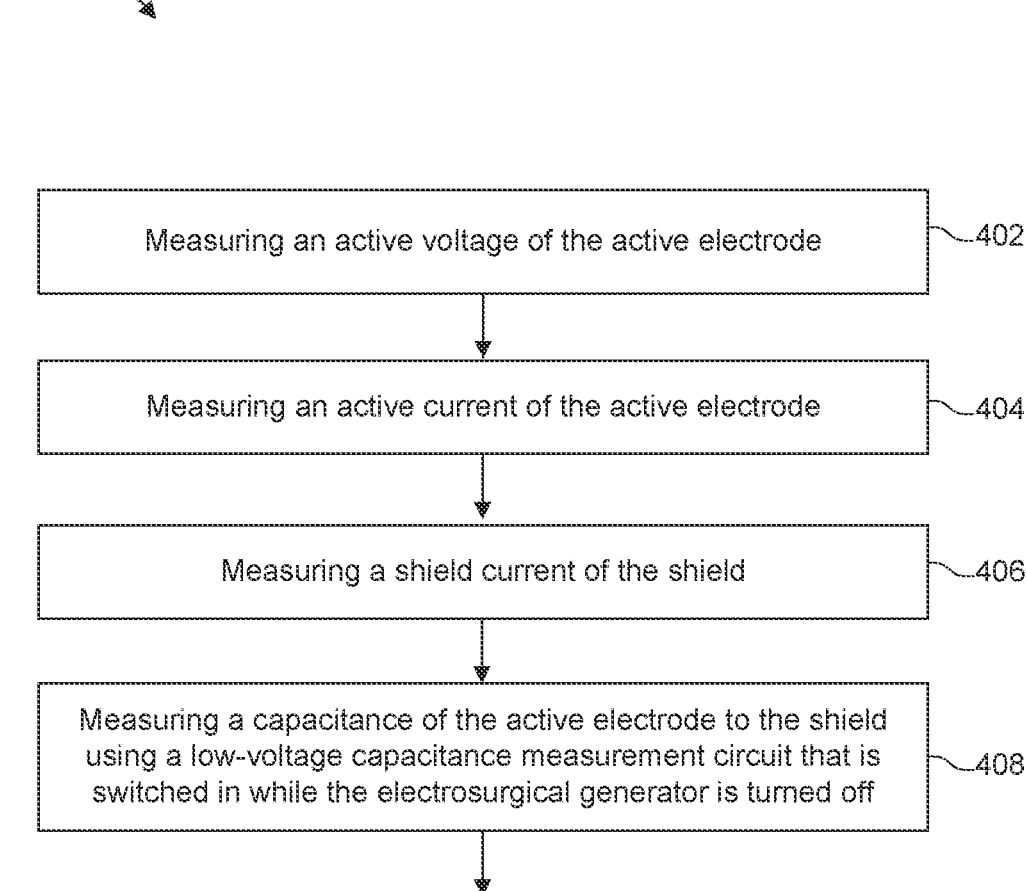
FIG. 4 is a flowchart illustrating a method of determining one or more electrical characteristics of the electrosurgical instrument in an example embodiment.

In step 304, the monitor 150 determines one or more electrical characteristics of the electrosurgical instrument 110. Step 304 comprises one or more steps described in FIG. 4. FIG. 4 is a flowchart illustrating a method of determining one or more electrical characteristics of the electrosurgical instrument 110 in an example embodiment. In step 402, the monitor 150 measures an active voltage of the active electrode 114. In step 404, the monitor 150 measures an active current of the active electrode 114. In step 406, the monitor 150 measures a shield current of the shield 116. In step 408, the monitor 150 measures a capacitance of the active electrode 114 to the shield 116 using a low-voltage capacitance measurement circuit (e.g., element 152/268) that is switched in while the electrosurgical generator 120 is turned off.

In step 410, the monitor 150 determines a parameter value of the electrosurgical instrument 110 based on a lookup table and a detected identifier of the electrosurgical instrument 110. For instance, in one embodiment, the parameter value is a capacitance value (and/or an equivalent parameter value which can be used to determine power drop) of the electrosurgical instrument 110 and cable as periodically measured by the monitor 150. Alternatively or additionally, the parameter value may comprise a capacitance value (and/or an equivalent parameter value which can be used to determine a power drop value) of the electrosurgical instrument 110 and cable as measured in a factory and stored in memory of the monitor 150.

Returning to FIG. 3, in step 306, the monitor 150 estimates a real power output of the active electrode 114 based on the one or more electrical characteristics of the electrosurgical instrument 110. For example, the monitor 150 may determine the estimated real power output of the active electrode in real-time based on power output by the electrosurgical generator and a power drop determined from one or more of: the active voltage, the active current, the shield current, the parameter value, and the capacitance of the active electrode to the shield. Alternatively or additionally, the monitor 150 may determine the estimated real power output at the electrode tip in real-time based on multiplying and averaging the active current and shield current.

In step 308, the monitor 150 displays the estimated real power output of the active electrode 114 of the electrosurgical instrument 110. The real load power displayed by the monitor 150 may or may not be the same as what is displayed or communicated by the generator 120 (e.g., depending on how the generator 120 is calculating its own output power). For instance, the capacitance to the shield, which is in parallel with the patient load (e.g., presumed to be resistive), may cause a reactive power drop that is not reflected in the estimated real power output.

Figure 5:
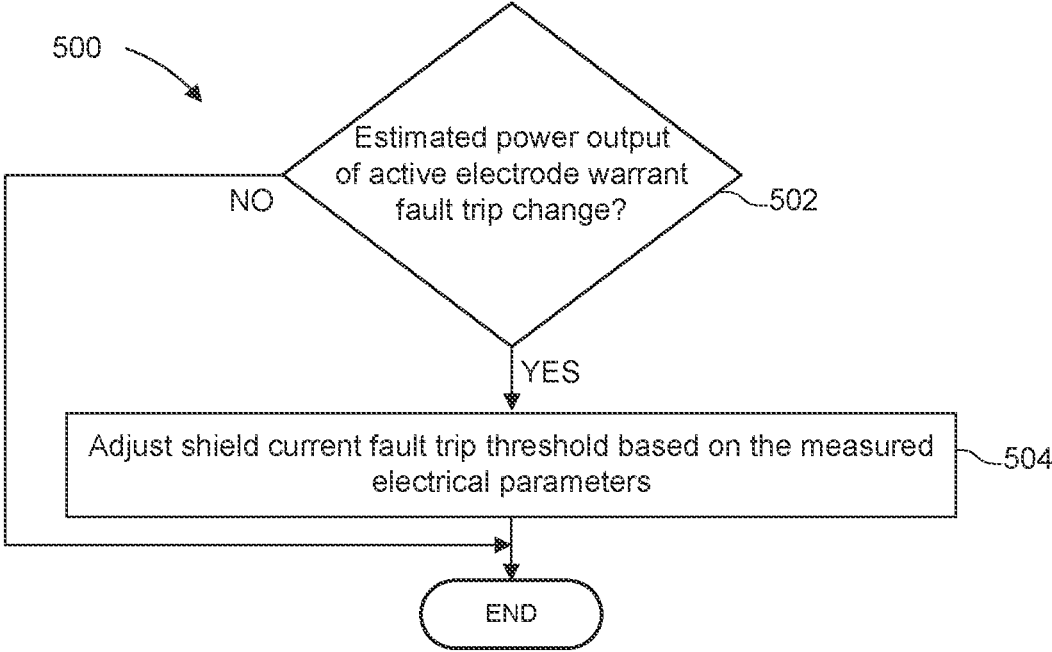
FIG. 5 is a flowchart illustrating a method of using an estimated power output of an active electrode to improve electrosurgical operation in an example embodiment.

FIG. 5 is a flowchart illustrating a method of using an estimated power output of an active electrode to improve electrosurgical operation in an example embodiment. In step 502, the monitor 150 determines whether an estimated power output of the active electrode 114 warrants a change in shield current fault threshold 294. If so, the method 500 proceeds to step 504, and the monitor 150 adjusts the shield current fault threshold 294 based on one or more measured electrical parameters (e.g., determined by one or more of steps 402-408). For example, the adjusting may be performed in response to determining that a capacitance value (e.g., total capacitance determined via one or more of steps 402-410) of the electrosurgical instrument 110 exceeds a threshold. Otherwise, if a change is determined not to be warranted in step 502, the method 500 skips step 504. Thereafter, the monitor 150 may continue to monitor electrical characteristics of the electrosurgical instrument 110 and perform one or more steps of the flowcharts described herein. That is, one or more steps of the flowcharts of FIGS. 3-5 may repeat to provide the step on a continuous or periodic basis.

Figure 6:
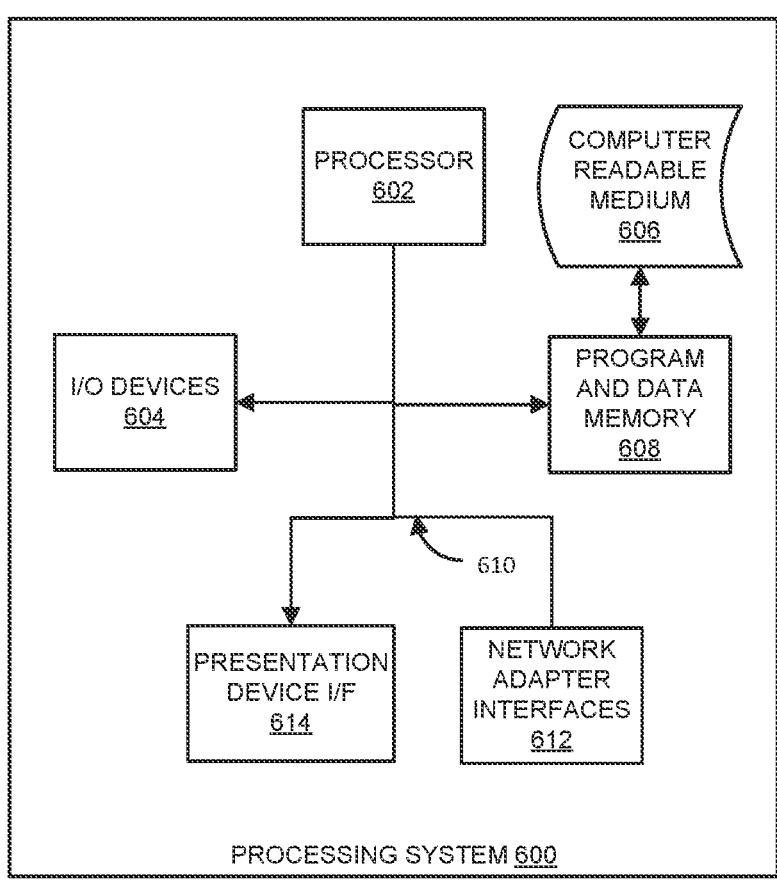
FIG. 6 illustrates a processing system operable to execute a computer readable medium embodying programmed instructions to perform desired functions in an example embodiment.

Although the electrosurgical functions described herein sometimes refer to laparoscopic tools and contexts, other electrosurgical procedures such as pelvoscopic, arthroscopic, thoroscopic, and the like may also apply. Embodiments disclosed herein can take the form of software, hardware, firmware, or various combinations thereof. In one particular embodiment, software is used to direct a processing system of the monitor 150/250 and/or generator 120/220 to perform the various operations disclosed herein. FIG. 6 illustrates a processing system 600 operable to execute a computer readable medium embodying programmed instructions to perform desired functions in an example embodiment. Processing system 600 is operable to perform the above operations by executing programmed instructions tangibly embodied on computer readable storage medium 606. In this regard, embodiments can take the form of a computer program accessible via computer readable medium providing program code for use by a computer or any other instruction execution system. For the purposes of this description, computer readable storage medium 606 can be anything that can contain or store the program for use by the computer.

Computer readable storage medium 606 can be an electronic, magnetic, optical, electromagnetic, infrared, or semiconductor device. Examples of computer readable storage medium 606 include a solid-state memory, a magnetic tape, a removable computer diskette, a random access memory (RAM), a read-only memory (ROM), a rigid magnetic disk, and an optical disk. Current examples of optical disks include compact disk-read only memory (CD-ROM), compact disk-read/write (CD-R/W), and DVD.

Processing system 600, being suitable for storing and/or executing the program code, includes at least one processor 602 coupled to program and data memory 608 through a system bus 610. Program and data memory 608 can include local memory employed during actual execution of the program code, bulk storage, and cache memories that provide temporary storage of at least some program code and/or data in order to reduce the number of times the code and/or data are retrieved from bulk storage during execution.

I/O devices 604 (including but not limited to keyboards, displays, pointing devices, etc.) can be coupled either directly or through intervening I/O controllers. Network adapter interfaces 612 may also be integrated with the system to enable processing system 600 to become coupled to other data processing systems or storage devices through intervening private or public networks. Modems, cable modems, IBM Channel attachments, SCSI, Fibre Channel, and Ethernet cards are just a few of the currently available types of network or host interface adapters. Display device interface 614 may be integrated with the system to interface to one or more display devices, such as screens for presentation of data generated by processor 602.

Although specific embodiments are described herein, the scope of the disclosure is not limited to those specific embodiments. The scope of the disclosure is defined by the following claims and any equivalents thereof.

What is claimed is:

1. An apparatus, comprising:

a monitor configured to be electrically coupled between an electrosurgical instrument and an electrosurgical generator, wherein the electrosurgical instrument includes an active electrode and shield, and wherein the monitor comprises one or more of:

measurement circuitry configured to measure at least one of: an active voltage of the active electrode, an active current of the active electrode, and a shield current of the shield; and identification circuitry configured to detect an identifier of the electrosurgical instrument, and to determine a parameter value corresponding with the identifier in a lookup table, and capacitance measurement circuitry configured to measure a capacitance of the active electrode to the shield, wherein the capacitance measurement circuitry is configured to be switched into an active line of the monitor while the electrosurgical generator is not being actively keyed, wherein the monitor includes a processor configured to determine an estimated real power output of the active electrode based on one or more of the active voltage, the active current, the shield current, the parameter value, and the capacitance of the active electrode to the shield, and wherein the monitor is configured to display the estimated real power output of the active electrode of the electrosurgical instrument, or is configured to send the estimated real power output to the electrosurgical generator to be displayed or processed.

2. The apparatus of claim 1, wherein:

the monitor is configured to adjust a fault trip threshold for the shield current of the electrosurgical instrument based on one or more of the active voltage, the active current, the shield current, and the parameter value.

3. The apparatus of claim 1, wherein:

the processor is configured to determine the estimated real power output of the active electrode in real-time based on power output by the generator and a power drop determined from one or more of: the active voltage, the active current, the shield current, the parameter value, and the capacitance of the active electrode to the shield; and the parameter value of the lookup table is a capacitance value of the electrosurgical instrument as periodically measured by the monitor.

4. The apparatus of claim 1, wherein:

the processor is configured to determine the estimated real power output of the active electrode by multiplying the active voltage and the active current together on a continuous or regularly-sampled basis and averaging a result of the multiplying.

5. A system for performing an electrosurgical procedure, the system comprising:

an electrosurgical generator;

an electrosurgical instrument comprising an active electrode and a shield, wherein the active electrode receives power provided by the electrosurgical generator; and a monitor configured to be electrically coupled between the electrosurgical instrument and the electrosurgical generator, to determine one or more electrical characteristics of the electrosurgical instrument, to estimate a real power output of the active electrode based on the determination of the one or more electrical characteristics, wherein the estimated real power output of the active electrode is determined based at least in part on a capacitance of the active electrode to the shield, and to display the estimated real power output of the active electrode of the electrosurgical instrument, wherein the determination of the one or more electrical characteristics comprises one or more of:

measure an active voltage of the active electrode;

measure an active current of the active electrode;

measure a shield current of the shield;

determine a parameter value of the electrosurgical instrument based on a lookup table and a detected identifier of the electrosurgical instrument; and measure the capacitance of the active electrode to the shield using a low-voltage capacitance measurement circuit that is switched in while the electrosurgical generator is turned off.

6. The system of claim 5, wherein:

the monitor is configured to adjust a fault trip threshold for the shield current of the electrosurgical instrument based on the one or more electrical characteristics.

7. The system of claim 5, wherein:

the monitor is configured to determine the estimated real power output of the active electrode in real-time based on power output by the electrosurgical generator and a power drop determined from one or more of: the active voltage, the active current, the shield current, the parameter value, and the capacitance of the active electrode to the shield.

8. The system of claim 5, wherein:

the monitor is configured to determine the estimated real power output of the active electrode by multiplying the active voltage and the active current together on a continuous basis and averaging a result of the multiplying.

9. The system of claim 5, wherein:

the parameter value of the lookup table is a capacitance value of the electrosurgical instrument as periodically measured by the monitor.

10. The system of claim 5 wherein:

the parameter value of the lookup table is a capacitance value or power drop value of the electrosurgical instrument as measured in a factory and stored in memory of the monitor.

11. A method of providing an accurate power estimate of a distal end of an electrosurgical instrument, the method comprising:

electrically coupling a monitor with the electrosurgical instrument, wherein the electrosurgical instrument includes an active electrode and a shield, and wherein the active electrode is configured to receive power from an electrosurgical generator;

determining, with the monitor, one or more electrical characteristics of the electrosurgical instrument, wherein the determining includes one or more of:

measuring an active voltage of the active electrode;

measuring an active current of the active electrode;

measuring a shield current of the shield;

determining a parameter value of the electrosurgical instrument based on a lookup table and a detected identifier of the electrosurgical instrument; and measuring a capacitance of the active electrode to the shield using a low-voltage capacitance measurement circuit that is switched in while the electrosurgical generator is turned off;

estimating a real power output of the active electrode based on the determining of the one or more electrical characteristics, wherein the estimated real power output is determined based at least in part on the capacitance of the active electrode to the shield; and displaying the estimated real power output of the active electrode of the electrosurgical instrument.

12. The method of claim 11, further comprising:

adjusting a fault trip threshold for the shield current of the electrosurgical instrument based on the one or more electrical characteristics.

13. The method of claim 11, further comprising:

determining the estimated real power output of the active electrode in real-time based on power output by the electrosurgical generator and a power drop determined from one or more of: the active voltage, the active current, the shield current, the parameter value, and the capacitance of the active electrode to the shield.

14. The method of claim 11, further comprising:

determining the estimated real power output of the active electrode by multiplying the active voltage and the active current together on a continuous basis and averaging a result of the multiplying.

15. The method of claim 11, wherein:

the parameter value of the lookup table is a capacitance value of the electrosurgical instrument as periodically measured by the monitor.

16. The method of claim 11, wherein:

the parameter value of the lookup table is a capacitance value or power drop value of the electrosurgical instrument as measured in a factory and stored in memory of the monitor.

* * * * *